United States Patent [19]

Mook et al.

[11] Patent Number: 4,628,360
[45] Date of Patent: Dec. 9, 1986

[54] METHOD AND APPARATUS FOR DETERMINING THE IMAGE TRANSFER QUALITY OF AN IMAGING SYSTEM

[75] Inventors: Adrianus Mook, Delft; Ronald J. Geluk, Nootdorp, both of Netherlands

[73] Assignee: N.V. Optische Industrie "De Oude Delft", Netherlands

[21] Appl. No.: 582,076

[22] Filed: Feb. 21, 1984

[30] Foreign Application Priority Data

Feb. 25, 1983 [NL] Netherlands ......................... 8300725

[51] Int. Cl.$^4$ ........................................... H04N 17/00
[52] U.S. Cl. ..................................... 358/139; 358/111
[58] Field of Search ......................... 358/10, 139, 111; 455/226

[56] References Cited

U.S. PATENT DOCUMENTS

| | | | |
|---|---|---|---|
| 3,683,282 | 8/1972 | D'Amato et al. ............... | 358/139 X |
| 3,825,835 | 7/1974 | Hammett et al. ............... | 358/139 X |
| 3,875,328 | 4/1975 | Gibson et al. ...................... | 358/139 |
| 3,995,105 | 11/1976 | Krivosheer et al. ................ | 358/139 |
| 4,170,025 | 10/1979 | Benkley et al. ..................... | 358/139 |
| 4,172,263 | 10/1979 | Tenten ................................ | 358/139 |
| 4,246,608 | 1/1981 | Baker ................................... | 358/139 |

OTHER PUBLICATIONS

"A New Random Noise Measuring Instrument for T.V. Signals;" 76, (1967.03), 180/182; Yamaguchi.

Primary Examiner—Howard W. Britton
Assistant Examiner—Victor R. Kostak
Attorney, Agent, or Firm—Louis E. Marn

[57] ABSTRACT

A method of, and apparatus for, determining the image transfer quality of an imaging system on the basis of the signal-to-noise ratio. A reference pattern comprising at least two different portions is presented to an input of the system. One portion provides a television output signal which is a measure for the noise, and another portion provides a television output signal comprising the same amount of noise in a combination with an image signal component. The television output signals are compared to determine the signal-to-noise ratio.

26 Claims, 8 Drawing Figures

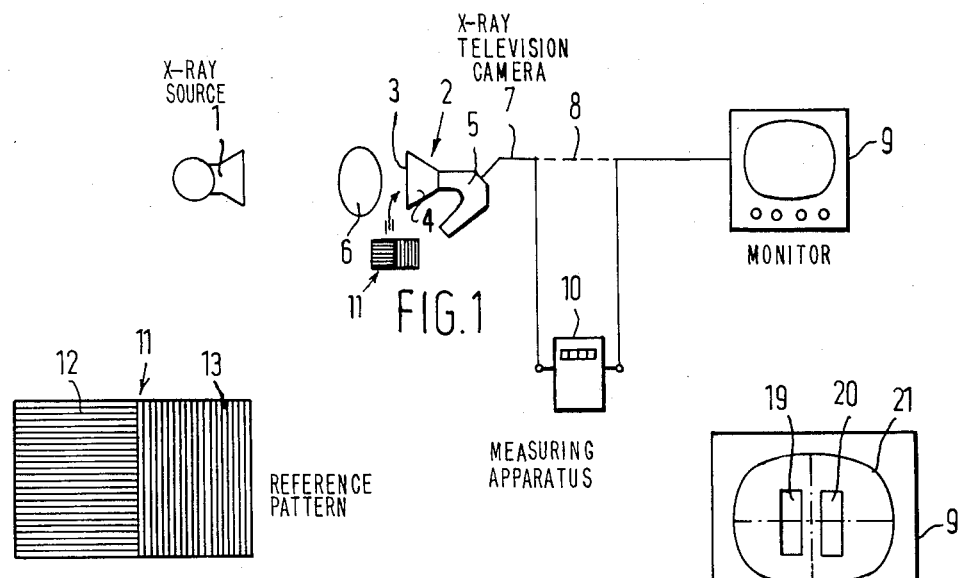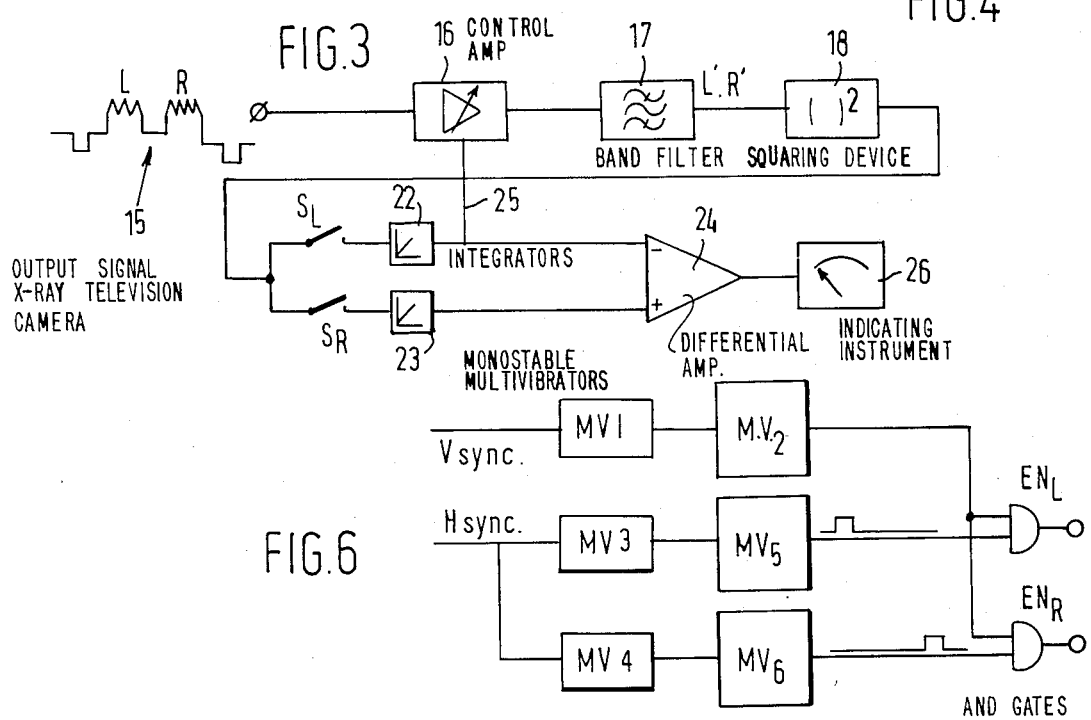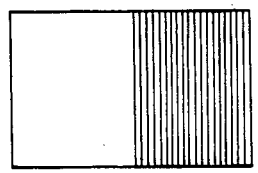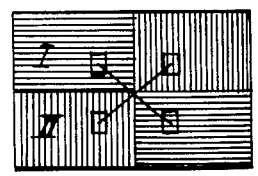

METHOD AND APPARATUS FOR DETERMINING THE IMAGE TRANSFER QUALITY OF AN IMAGING SYSTEM

This invention relates to a method of, and apparatus for, determining the image transfer quality of an imaging system on the basis of the signal-to-noise ratio, in which a television signal is formed.

In practice there is a need for a possibility of measuring the image transfer quality of imaging and image transferring apparatuses of diverse kinds in a simple and rapid manner.

Imaging and image transferring apparatuses, as used herein, means any apparatus forming an image or forming electrical signals representing an image, and which can be converted into a video picture. Some examples of such apparatuses are lens systems, slide projectors, television cameras, X-ray television cameras, night viewing apparatus, video recorders, and also apparatus in which an image is formed by means of a computer, as is the case, for example, with the so-called CT-apparatus (Computerized Tomography), and in the study of nuclear magnetic resonance phenomena.

In the case of the above and other imaging and image transferring apparatuses, there is a need, both during manufacture and later during use, for a possibility of measuring the image transfer quality. In the past, this has often been done visually. This has the disadvantage that the human eye is not very sensitive to relatively small differences in quality. Also, it is difficult to compare visual observations with each other if there is a certain time lapse between the observations.

If, for example, during the servicing of an overhead projector the surface for supporting the original to be projected is cleaned, this provides an improvement of the image projected, which, however, is difficult to perceive visually. If, subsequently, the mirrors are cleaned, this by itself again provides an improvement that is difficult to perceive visually. The combination of several minor improvements, however, may result in a clear visual improvement. The result is that the cause of the deterioration in image transfer quality is difficult to trace.

The same applies to other imaging and image transferring systems.

It is an object of the present invention to satisfy the need outlined above.

To this effect, according to the invention, a method of the kind described is characterized by presenting to an input of the system a reference pattern comprising at least two different portions, one portion providing a television output signal which is a measure for the occurrent noise, and another portion providing a television output signal comprising the same amount of occurrent noise in a combination with an image signal component; and comparing the television output signal associated with said one portion of the reference pattern with the television output signal associated with said other portion of the reference pattern to determine the signal-to-noise ratio.

An apparatus of the kind described is characterized, according to the invention, by a reference pattern comprising at least two different portions corresponding to distinct regions of the television signal; and by a measuring device connected to the output of the system to be tested, said measuring device including means for generating measuring fields corresponding to said different portions of the reference pattern, or to parts of said different portions, and means for separating the portions of the output signal of the television signal generator associated with said measuring fields from the output signal of the television signal generator and comparing said portions with one another to determine the signal-to-noise ratio.

It is noted that the present invention uses a television signal. This can be formed by scanning as occurs in a television camera, but also, for example, in a computer.

In some cases, it is possible to use a television signal generator already present in the system being tested. In other cases, there is no such television signal generator in the system being tested. This is the case, for example, in slide, film, and overhead projectors. It that case, it is necessary to use a separate television camera.

The invention will be described in more detail hereinafter with reference to an embodiment adapted to perform measurements in an X-ray television camera. This is an apparatus comprising an X-ray screen which converts incident X-ray radiation into light, and further includes a video pick-up tube which scans the X-ray screen and converts the light image formed by the X-ray screen into television signals that can be supplied to a video monitor in order that the light image formed by the X-ray screen may be rendered accessible for direct observation. The combination of X-ray screen and video pick-up tube is generally called an X-ray television camera.

It is explicitly noted that the invention offers countless other applications, and that the following detailed description and the accompanying drawings are given merely as a non-limitative example of how the invention can be applied and embodied.

FIG. 1 shows diagrammatically an apparatus for X-raying an object;

FIG. 2 diagrammatically shows an example of a reference pattern suitable for use in the method according to the invention;

FIG. 3 shows diagrammatically one embodiment of an apparatus for applying the method according to the invention;

FIG. 4 illustrates a measuring field configuration suited to the reference pattern of FIG. 2 in relation to the screen of a video monitor;

Figure 5:
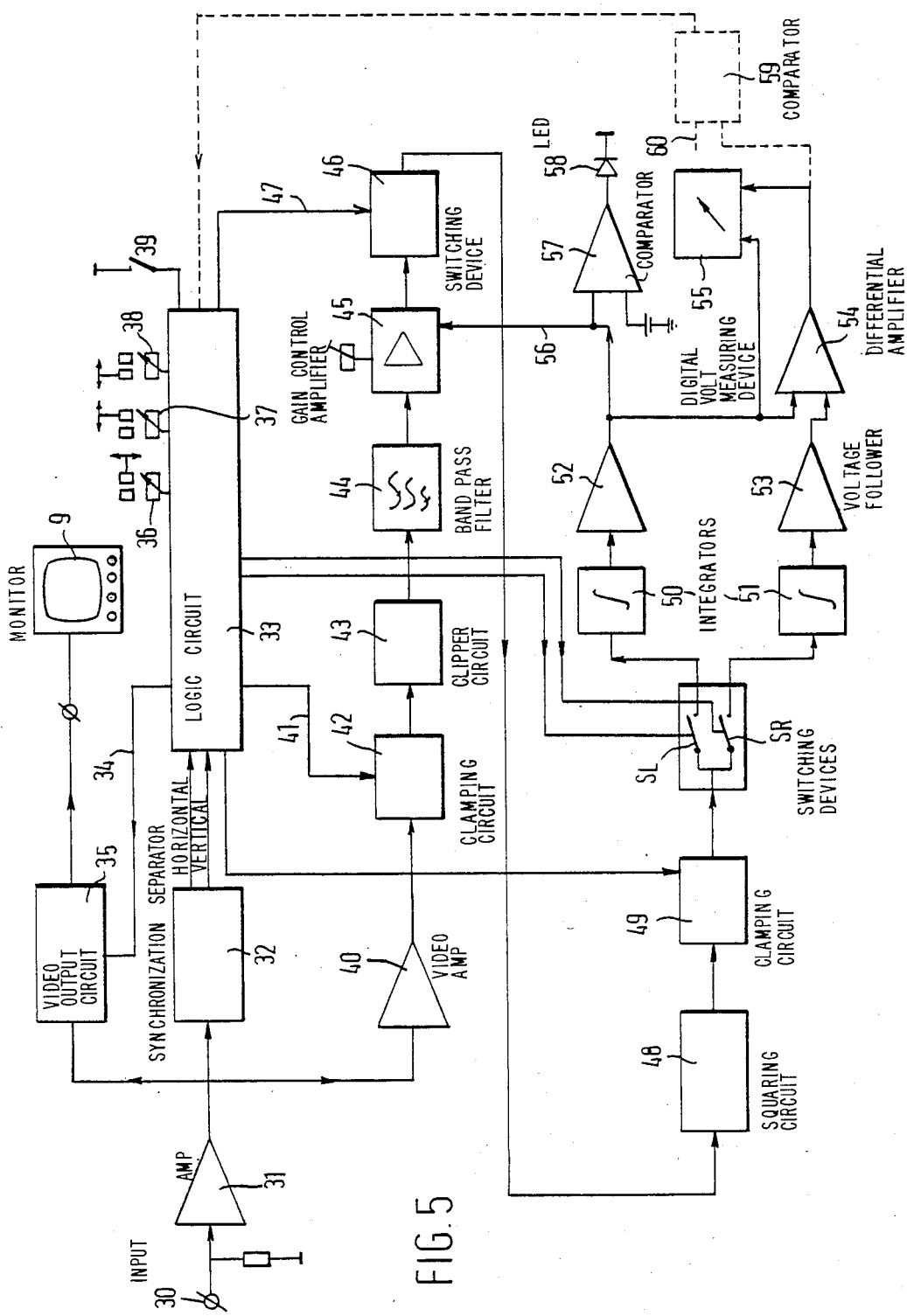
FIG. 5 shows diagrammatically and in greater detail an embodiment of an apparatus according to the invention.

FIG. 6 diagrammatically shows an example of a measuring field generator circuit that can be used in the apparatus of FIG. 3;

FIG. 7 shows one variant of the reference pattern of FIG. 3; and

FIG. 8 shows another variant of the reference pattern of FIG. 3.

FIG. 1 diagrammatically shows an apparatus for X-raying an object. This may be a patient or a part of the patient's body. The apparatus comprises an X-ray source 1 and an X-ray television camera placed in the field of radiation of the X-ray source, which camera is shown at 2 and comprises an X-ray screen 3 which, by means of a light-tight housing 4, is connected to a video pick-up tube 5. An article or patient 6 to be X-rayed can be placed between the X-ray source 1 and the X-ray screen 3.

The light image which, during operation, is formed at the side of the X-ray screen 3 remote from the object or the patient 6 is scanned by the video pick-tube 5 and supplied, in the form of electric video signals, via a line 7 to a video monitor 9. Line 7 comprises a portion 8, shown dotted in the figure, that can be replaced by a signal-to-noise meter 10 according to the present invention.

The image visible on monitor 9 always contains a certain amount of noise which may have an adverse effect on image quality. This noise is caused by the electrical components of the apparatus, the X-ray screen, the pick-up tube, and the article being X-rayed. Furthermore, the amount of noise is affected by the X-ray dose being used.

By means of statistical calculations, the noise contribution of most of the elements of the apparatus shown in FIG. 1 can be predicted rather accurately.

The applicants have found, however, that in practice the actual signal-to-noise ratio of such an apparatus can deviate considerably from the signal-to-noise ratio calculated.

As the signal-to-noise ratio of the television signal determines to a large extent the quality of the apparatus, it is of importance that the noise contribution, or the signal-to-noise ratio of an X-ray television camera can be measured in a simple and rapid manner. In such a measurement, the variable influence of the objects to be X-rayed should be eliminated.

According to the invention, for such a measurement, use is made of a reference pattern 11 with a special configuration, and of an electrical measuring apparatus 10 which is connected between the X-ray camera and the monitor.

The reference pattern, sometimes referred to as a phantom, is placed, in the same way as an object being X-rayed, in front of the X-ray screen of the X-ray television camera and successively X-rayed with different, pre-determined dosages of radiation. The measuring apparatus 10, which will be described in greater detail hereinafter, indicates the signal-to-noise ratio with each of the dosages of radiation used, so that a curve can be made which indicates the relationship between the X-ray dosage and the signal-to-noise ratio, and which is a measure for the quality of the X-ray television camera.

The reference pattern has been designed so that it comprises at least two different portions which correspond to distinct portions of the monitor image, one portion of the reference pattern providing a signal at the output of the measuring apparatus, which only represents the occurrent noise, while the other portion provides a signal which comprises the occurrent noise together with an image signal component representing this portion of the reference pattern.

FIG. 2 shows an embodiment of such a reference pattern. The reference pattern 11 shown comprises a screen which in the left-hand portion 12 has narrow horizontal strips, and in the right-hand portion 13 narrow vertical strips, of a material attenuating X-ray radiation. The screen may be self-supporting, but also be applied to a basis of a material which attenuates X-ray radiation to a considerably lesser extent.

For the performance of test measurements, we successfully used a pertinax base plate, on which the screen lines were made by means of soldering wire.

For the measurement, the reference pattern is placed approximately centrally in front of the X-ray screen, so that the picture of the reference pattern occupies the central part of the monitor image.

The left-hand portion 12 and the right-hand portion 13 of the reference pattern thus formed are designed so that an equal attenuation is obtained, so that the video signal associated with the left-hand portion (i.e. the output signal from the X-ray television camera) has the same level as the video signal associated with the right-hand portion.

If desired, in order to produce a sufficiently low signal level, corresponding to the normal operating levels, and which contains relatively much noise, an additional attenuating element, in the form of, for example, a lead plate, may be placed between the X-ray source and the X-ray television camera.

The left-hand half of the reference pattern shown gives rise to a video signal comprising a noise component, a DC voltage component, and a low-frequency component with a frequency in the order of the video line frequency. The low-frequency component is caused by the horizontal strips of the raster.

The right-hand half of the reference pattern shown gives rise to a video signal comprising a noise component, a DC voltage component, and a high-frequency component. The high-frequency component is caused by the vertical strips of the right-hand portion of the reference pattern. By a suitable selection of the interval of the vertical strips a frequency of, for example, 1 MHz can be obtained.

By separating the signal portion associated with the left-hand portion of the reference pattern from the signal portion associated with the right-hand portion of the reference pattern, and passing these signal portions, either before or after their separation, through a band filter having a pass band of, for example, between 0.7 and 2.4 MHz, two signals are formed. Of these, one signal, associated with the left-hand portion of the reference pattern, only comprises a noise component (N) whereas the other signal, associated with the right-hand portion, comprises a noise component (N) plus an image signal component (S). It is on the basis of these two signals that the signal-to-noise ratio can be determined.

As, for each measurement, the same reference pattern is used and the same dosage of radiation can be used, the signal-to-noise ratio determined in this manner is a measure for the quality of the X-ray television camera.

All this can be realized by means of the measuring apparatus shown by way of example, and diagrammatically, in FIG. 3.

The output signal from the X-ray television camera, shown schematically at 15, is supplied to a control amplifier 16, the function of which will be described hereinafter. The output signal from the control amplifier is supplied to a band filter 17 with a pass band of, for example, between 0.7 and 2.4 MHz, so that the low frequencies resulting from the structure of the left-hand half of the reference pattern, and which occur in the portion of the signal 15 designated by L are blocked. In this way, a video signal is produced with a portion L' containing noise only, and a portion R' containing noise and a signal component of relatively high frequency, so that L'=noise and R'=noise+hf signal. It is noted that the terms "high-frequency" and "low-frequency" in this connection have a relative meaning and are related to the reference pattern. Relative to the frequencies normally occurring in a video signal, the high-frequency signal component does not in fact have a particularly high frequency.

For the absolute amplitudes of these signals, the following equations apply:

$$L' = \sqrt{(\text{noise})^2} \quad \text{and} \quad R' = \sqrt{(\text{noise})^2 + (\text{h.f. signal})^2}$$

The video signal is therefore squared by means of a squaring device 18, so that the output signal of the squaring device comprises a portion $L'^2=(\text{noise})^2$ and a portion $R'^2=(\text{noise})^2+(\text{h.f. signal})^2$.

This squared signal is supplied to a pair of parallel-connected switching devices $S_L$ and $S_R$. The switching device $S_L$ is only open during the time when the video signal offered corresponds to the left-hand half of the reference pattern, or a part of this period.

Similarly, the switching device $S_R$ is only open during the time (or a part thereof) when the video signal offered corresponds to the right-hand half of the reference pattern.

The switching devices define in fact two measuring fields which can be shown on the monitor, in a manner not shown, and for example may have a location and dimensions as shown in FIG. 4 at 19 and 20 on the screen 21 of monitor 9.

For the realization of such measuring fields, switching devices $S_L$ and $S_R$ should be open during a number of video lines for a fixed interval $\tau$, beginning a fixed period after the beginning of the video line, and this for a number of lines corresponding to the desired vertical dimensions of the measuring field. This vertical dimension is preferably smaller than corresponds to the vertical dimension of the reference pattern.

Concomitant with each video line comprised by the measuring field, switching device $S_L$ is opened a short time after the closing of switching device $S_L$, and remains open during the interval $\tau$. As a consequence the measuring fields are spaced some distance apart in the horizontal direction, and the central transitional portion of the reference pattern falls outside the measuring fields, so that transitional effects are avoided.

The output voltages of switching devices $S_L$ and $S_R$ are supplied to an associated integrator 22, 23, respectively, which as its output signal produces a DC voltage proportional to $(\text{noise})^2$ and $(\text{noise})^2+(\text{h.f. signal})^2$, respectively. These DC voltages are respectively supplied to the negative and positive inputs of a differential amplifier 24, so that its output signal is proportional to $(\text{h.f. signal})^2$.

By dividing this signal by the signal presented as the negative input of differential amplifier 24, and extracting the square root from the result obtained, the signal-to-noise ratio (S/N) can be determined.

In the apparatus shown in FIG. 3, a slightly different method has been followed in that, by means of control amplifier 16, the control input of which is connected via a line 25 to the output of integrator 22, the video signal is regulated so that the noise voltage is constant. Consequently, the output signal of the differential amplifier 24 is a direct measure for the ratio $(S/N)^2$, and hence also for the ratio (S/N).

Accordingly, in the embodiment of FIG. 3, the output signal from the differential amplifier is supplied directly to an indicating instrument 26, for example, a digital volt meter.

For the sake of completeness, the apparatus of FIG. 3 is shown in the form of a more detailed block scheme in FIG. 5, which also indicates the components for control.

The apparatus shown in FIG. 5 comprises an input 30, to which, in operation, the electric signals from the X-ray television camera are supplied. Input 30 is connected to an amplifier 31 serving for impedance-adaptation.

The output of amplifier 31 is connected to a synchronisation separator 32 which separates the synchronisation pulses present in the video signal. The synchronisation separator has two outputs, one of which provides the vertical synchronisation pulses, and the other the line synchronisation pulses, i.e., both the horizontal and the vertical synchronisation pulses, to a logic circuit 33.

Starting from the synchronisation pulses supplied, the logic circuit 33 forms switching pulses for forming the measuring fields and controlling the switching devices $S_L$ and $S_R$. For this purpose the logic circuit 33 is connected via a line 34 to an input of a video output circuit 35, which is also connected to the output of the input circuit, and the output of which is connected to the monitor 9. The output signal of the video output circuit 35 accordingly comprises both video information and information defining the measuring fields, so that the measuring fields can be rendered visible on the monitor. The measuring fields may, for example, be 3.3 milliseconds high, 7 $\mu$seconds wide, and be spaced apart a distance of 5 $\mu$seconds.

The logic circuit preferably comprises control elements 36, 37 and 38 for shifting the measuring fields, and a switch 39 for interchanging the measuring fields.

The output signal of input circuit 31 is further supplied to a second video amplifier 40, which is connected to a clamping circuit 42 which under the control of clamping pulses provided by the logic circuit 33 via a line 41 sets the black level of the video signal at a desired value, for example, 0 volt. The clamping circuit is followed by a clipper circuit 43, which removes the synchronisation pulses from the video signal. The resulting signal is supplied to a band pass filter 44 which, as described with reference to FIG. 3, blocks the low frequencies. The output signal from the band filter is supplied to a gain-control amplifier 45, which keeps the noise level (N) at a constant level, so that the ultimate signal level (S) is a direct measure for the signal-to-noise ratio S/N.

The output signal from gain-control amplifier 45 is supplied to a switching device 46 serving to eliminate spurious pulses that could still be present in the signal as a result of the blanking and the original synchronizing pulses. The device 46 is controlled by pulses provided by the logic circuit 33 via a line 47.

The switching device 46 is followed by a squaring circuit 48 which comprises a multiplier whose inputs are connected in parallel.

The output signal from the squaring circuit 48 is supplied via a clamping circuit 49, serving to recover the zero reference of the squared signal, and controlled by a clamping pulse generated in the logic circuit 33, to switching devices $S_L$ and $S_R$. These split the signals associated with the respective left-hand and right-hand measuring fields in the manner described. The switching devices are controlled by signals from the logic circuit 33.

The signals passed by $S_L$ and $S_R$, respectively, are integrated for a certain period of time, in the manner described, by means of integrators 50 and 51, respectively, which are followed by voltage followers 52, 53.

The output signals from the voltage followers are DC voltages, whose values represent the noise level $(N)^2$ and the signal level $(S)^2+(N)^2$, respectively.

These output signals are respectively supplied to the negative and the positive input of a differential amplifier 54, so that the output signal from the differential amplifier represents the signal level $(S)^2$.

This output signal is supplied to a digital volt measuring device 55 whose reading is representative of the ratio of $(S/N)^2$.

The output signal from voltage follower 52 is also used to control the control amplifier 45 via a line 56. If the signal supplied to input 30 is insufficient, a good S/N measurement is impossible. Determinative of this is the noise level at the input and hence the output signal of the voltage follower 52. This output signal is accordingly supplied to comparator 57, which issues an output signal energizing a LED 58 if the noise level decreases below a pre-determined reference value.

The circuits referred to hereinbefore can all be built up using commercially available circuits.

FIG. 6 shows an example of a logic circuit for generating the pulses defining the measuring fields and controlling the switching devices $S_L$ and $S_R$.

The vertical synchronisation pulses control a first monostable multivibrator $MV_1$, which in response to each vertical synchronisation pulse issues an output pulse terminating at the moment when the measuring field should begin in the vertical direction.

The trailing edge of the output pulse from $MV_1$ activates a second monostable multivibrator $MV_2$, which issues a pulse whose duration determines the vertical dimension of the measuring field.

The horizontal synchronisation pulses activate a third monostable multivibrator $MV_3$ and a fourth monostable multivibrator $MV_4$, which each issue an output pulse in response to each horizontal synchronisation pulse.

The output pulse from $MV_3$ terminates at the moment when, in a horizontal direction, the left-hand measuring field should begin, while the output pulse from $MV_4$ terminates at the moment when, in a horizontal direction, the right-hand measuring field should begin.

The trailing edges of the output pulses from $MV_3$ and $MV_4$ activate a monostable multivibrator $MV_5$ and $MV_6$, respectively, which issue a pulse whose duration corresponds to the width of the left-hand and right-hand measuring field, respectively.

The output pulses from $MV_5$ and $MV_6$ should only be transmitted if the output pulse from $MV_2$ is present. For this purpose there are provided AND gates $EN_L$ and $EN_R$.

It is noted that the apparatus described is only an example of a possible arrangement for the application of the method according to the invention. Various modifications of the circuitry described and of the reference pattern described will readily occur to those skilled in the art.

Thus, for example, the reference pattern may be turned through 180°, so that the signal associated with the left half contains the high-frequency component. In practice this can be utilized to determine whether the signal-to-noise ratio is equal for the two halves of the picture.

Furthermore, the left half of the reference pattern shown is only provided with horizontal strips to produce an attenuation that is equal to that of the right half. This, however, can also be effected, for example, using a plate of X-ray radiation attenuating material that provides a total attenuation equal to that of the right half of the reference pattern. Such a reference pattern is shown in FIG. 7.

Also, the left half of the reference pattern need not be continuous with the right half, but there may be an interspace slightly narrower than the distance corresponding to the distance between the left-hand and the right-hand measuring field.

Furthermore, the reference pattern may consist of four quadrants, for example, as shown in FIG. 8, in order that differences in the signal-to-noise ratio between the upper and lower picture halves may be measured direct. For this purpose, switching commands have to be generated in the circuit of FIG. 3 and FIG. 5, corresponding to the location of the measuring quadrants.

Furthermore, the reference pattern may have a certain non-negligible thickness, so that there is a three-dimensional pattern.

It is further observed that the design of the reference pattern depends on the nature of the imaging system to be tested. In the application described above, in which an X-ray television circuit was tested, the reference pattern should be made using material, such as lead, which attenuates X-ray radiation. The patterns of FIG. 2 and FIG. 8 are then built up, for example, from strips of lead fitted in, or on, for example a support of synthetic plastic s material.

For testing, for example, an overhead projector, the reference pattern may be a line pattern depicted on a transparent material or, for the left-hand of a pattern as shown in FIG. 7, a uniform blacking. The pattern is then put on the glass plate of the overhead projector and the projector's image is observed by means of a video camera coupled to the measuring apparatus of the present invention.

For testing apparatus in which an image is formed by means of a computer, the reference pattern is generated or stored electronically so that it is not necessary to have a physical reference pattern.

With regard to the determination of the S/N ratio it is further noted that it is also possible to use the differential signal (output signal from the differential amplifier 54) for controlling the width of at least one of the measuring fields. In such a method the widths of the measuring fields are controlled electronically (via the logic circuit 33) until a predetermined "S/N value" is reached. For this purpose a comparator may be used, shown dotted in FIG. 5 at 59, one input of which is connected to the output of the differential amplifier 54, and the pre-determined reference "S/N value" is supplied to another input 60.

The actual S/N value is then determined by comparing the area ratios of the resulting measuring fields. This comparison can be effected purely electronically, but it is equally possible to reproduce the resulting measuring fields on a monitor and to measure their dimensions to arrive at the desired result.

These and similar modifications will readily occur to those skilled in the art without departing from the scope of the present invention.

We claim:

1. A method of determining the image transfer quality of an imaging system on the basis of signal-to-noise ratio and including forming a television signal, characterized by: presenting to an input of said imaging system a reference pattern comprising at least two different portions, one portion of said reference pattern resulting, after formation of said television signal, in a first section of image carrying information of a television output signal and being a measure for occurrent noise, and another portion of said reference pattern resulting, after formation of said television signal, in a second section of image carrying information of said television output signal and comprising a like amount of said occurrent noise in combination with an image signal component; and comparing said first section of image carrying information associated with said one portion of said reference pattern with said second section of image carrying information associated with said other portion of said reference pattern to generate a signal-to-noise ratio.

2. The method according to claim 1, characterized in that said two portions of said reference pattern comprise identical structures situated so that said one portion of said reference pattern results in a low-frequency image signal component in said television output signal removed by a filter, and said another portion of said reference pattern results in a high-frequency image signal signal component in said television output signal.

3. The method according to claim 1 and further including the step of supplying said television output signal to a measuring device, said measuring device comprising first switching means for separating from said television output signal a first signal portion corresponding with said one portion of said reference pattern; and a second switching means for separating from said television output signal a second signal portion corresponding to said another portion of said reference pattern.

4. The method according to claim 3 wherein said separated first and second signal portions are each corresponding to a measuring field, and further including the step of reproducing said measuring fields.

5. The method according to claim 4 wherein said measuring fields are of equal areas.

6. The method according to claim 4 wherein said measuring fields are bounded by same lines of said television output signal.

7. The method according to claim 3 and further including the steps of integrating output signals from said switching means to produce a first DC voltage signal representing said occurrent noise and a second DC voltage signal representing said occurrent noise in combination with an image signal; and deducting said first DC voltage signal from said second DC voltage signal to produce a differential signal representative of said image signal.

8. An apparatus for determining the image transfer quality of an imaging system on the basis of signal-to-noise ratio and including a television signal generator which comprises a reference pattern having two different portions corresponding to distinct regions of a television output signal to be generated, said reference pattern being presented to said television signal generator; and a measuring device connected to said television output signal of such imaging system, said measuring device including means for generating measuring fields corresponding to said different portions of said reference pattern, means for separating said portions of said television output signal of said television signal generator associated with said measuring fields from said television output signal of said television signal generator and means for comparing said portions to determine signal-to-noise ratio.

9. The apparatus according to claim 8 wherein said reference pattern comprises at least two portions, including a first portion homogenous throughout its entire area and not resulting in an AC signal component, and a second portion having a structure resulting in a high-frequency image signal component.

10. The apparatus according to claim 8, characterized in that said reference pattern comprises at least two portions each built up from substantially parallel strips, including a first portion in which said parallel strips are parallel to television lines of said television signal generator and only result in a low-frequency image signal component, and a second portion in which said parallel strips intersect said television lines and result in a high-frequency image signal component, said first and said second portion otherwise having the same characteristics.

11. The apparatus according to claim 8, characterized in that said reference pattern comprises four quadrants including two diagonally opposed quadrants of said reference pattern built up on strips intersecting television lines of said television signal generator and result in a high-frequency image signal component, and two other diagonally opposed quadrants not resulting in a high-frequency image signal component.

12. The apparatus according to claim 11, characterized in that said two other diagonally opposed quadrants are built up of strips parallel to said television lines and result in a low-frequency image signal component.

13. The apparatus according to claim 8, wherein said measuring device comprises a band filter, said band filter passing said high-frequency component caused by the referenced pattern in said output signal from said television signal generator and blocks said low-frequency component caused by said reference pattern in said television output signal of said television signal generator.

14. The apparatus according to claim 13 and further including at least two switch means controlled by said means for generating measuring fields whereby each of said switch means is only opened so long as said television output signal of said television signal generator corresponds to an associated measuring field.

15. The apparatus according to claim 14 and further including a first integrator wherein an output of one of said switch means is connected and a second integrator wherein an output of said other switch means is connected for forming, respectively, a first DC voltage corresponding to a measuring field corresponding to a reference pattern portion built up from strips intersecting television lines of said television signal generator, and a second DC voltage corresponding to a different reference pattern portion.

16. The apparatus according to claim 15 and further including a differential amplifier wherein said first DC voltage is supplied to a positive input of said differential amplifier, and said second DC voltage is supplied to a negative input of said differential amplifier; and wherein an output signal of said differential amplifier is divided by a second DC voltage and is supplied to an indicating instrument.

17. The apparatus according to claim 15 and further including a control amplifier to receive said television output signal from said television signal generator prior to said switch means, said control amplifier being controlled by said second DC voltage to maintain same at a constant level; and a differential amplifier having a positive input to which said first DC voltage is supplied, said second DC voltage being supplied to a negative input of said differential amplifier, and wherein an output signal from said differential amplifier is supplied to an indicating instrument.

18. The apparatus according to claim 14 wherein said measuring device includes a squaring device preceding said switch means.

19. The apparatus according to claim 14 wherein said switch means are controlled so that said measuring fields do not overlap.

20. The method according to claim 1, characterized by using: a measuring device to which said television output signal is supplied and comprises a first switching means for separating from said television output signal a first signal portion corresponding to said one portion of said reference pattern and a second switching means for separating from said television output signal a second signal portion corresponding to said other portion of said reference pattern, said separated signal portions each corresponding to a measuring field; a monitor connected to said measuring device for reproducing said measuring fields, output signals from said switching means being integrated to produce a first DC voltage signal representing said occurrent noise and a second DC voltage signal representing said occurrent noise in combination with an image signal, said first DC voltage signal being deducted from said second DC voltage signal to produce a differential signal representing said image signal; said differential signal for controlling dimensions of said measuring fields until a predetermined reference value of a ratio between said television output signal associated with said one portion of said reference pattern and said television output signal associated with said other portion of said reference pattern is obtained; and thereafter determining actual signal-to-noise ratio by a ratio of surface areas of said measuring fields.

21. The method according to claim 20, characterized by said reference pattern having a contrast for X-ray radiation.

22. The method according to claim 20, characterized by said reference pattern optically affecting observable radiation.

23. The method according to claim 20 wherein said reference pattern is electronically generated in said imaging system.

24. The apparatus according to claim 17 and further including a comparator connected to the output of the differential amplifier, said comparator having a reference input and an output connected to means for regulating area of at least one of the measuring fields.

25. The reference pattern used in the method according to claim 21, characterized by a carrier transparent to radiation to which said imaging system being examined is sensitive, said carrier comprising at least one first portion having strips of a material attenuating said radiation, and of at least one second portion of the same area as said first portion and also having strips of material attenuating said radiation, said strips of said first portion and said strips of said second portion being at right angles to each other, said attenuation caused by said joint strips of said first portion being equal to said attenuation caused by said joint strips of said second portion.

26. The reference pattern for use in the method according to claim 21, characterized by a carrier transparent to radiation to which said imaging system being tested is sensitive, said carrier comprising at least one first portion including strips of a material which attenuates said radiation and at least one second portion of the same area as said first portion, said second portion attenuating said radiation substantially uniformly throughout its entire surface, said attenuation caused by said joint strips of said first portion being equal to said attenuation caused by said second portion.

* * * * *